US010625057B2

(12) United States Patent
Weiss

(10) Patent No.: US 10,625,057 B2
(45) Date of Patent: Apr. 21, 2020

(54) SAFETY CLIP FOR SELDINGER CANNULA

(71) Applicant: B. BRAUN MELSUNGEN AG, Melsungen (DE)

(72) Inventor: André Weiss, Guxhagen (DE)

(73) Assignee: B. Braun Melsungen AG (DE)

(*) Notice: Subject to any disclaimer, the term of this patent is extended or adjusted under 35 U.S.C. 154(b) by 407 days.

(21) Appl. No.: 14/911,490

(22) PCT Filed: Aug. 7, 2014

(86) PCT No.: PCT/EP2014/067008
§ 371 (c)(1),
(2) Date: Feb. 11, 2016

(87) PCT Pub. No.: WO2015/022260
PCT Pub. Date: Feb. 19, 2015

(65) Prior Publication Data
US 2016/0184556 A1 Jun. 30, 2016

(30) Foreign Application Priority Data
Aug. 15, 2013 (DE) .................. 10 2013 216 228

(51) Int. Cl.
A61M 25/09 (2006.01)
A61M 5/32 (2006.01)
A61M 25/06 (2006.01)

(52) U.S. Cl.
CPC .... *A61M 25/09041* (2013.01); *A61M 5/3245* (2013.01); *A61M 5/3273* (2013.01); *A61M 25/0618* (2013.01); *A61M 25/0631* (2013.01); *A61M 25/0606* (2013.01); *A61M 25/09* (2013.01)

(58) Field of Classification Search
CPC .......... A61M 25/0618; A61M 25/0169; A61M 25/0612; A61M 25/0631; A61M 25/0606; A61M 25/09; A61M 2005/325; A61M 5/3273; A61M 25/09041; A61M 5/3245; A61M 2005/14256; A61M 2005/1426;
(Continued)

(56) References Cited

U.S. PATENT DOCUMENTS 5,419,766 A * 5/1995 Chang ................. A61M 5/3273
604/110
5,512,052 A * 4/1996 Jesch ................. A61B 17/3415
604/158

(Continued)

FOREIGN PATENT DOCUMENTS

DE 10 2008 045 692 A1 3/2010
EP 2 134 394 B1 2/2012

OTHER PUBLICATIONS

International Search Report and Written Opinion of the International Search Report for PCT/EP2014/067008 dated Nov. 17, 2014.

*Primary Examiner* — Brandy S Lee
*Assistant Examiner* — Hong-Van N Trinh
(74) *Attorney, Agent, or Firm* — RatnerPrestia

(57) ABSTRACT

The invention relates to a cannula, having an elongated tube, open on both ends, for receiving an elongated element and a movable safety clip enclosing the tube which encloses the tube end when advancing along the tube beyond one of the two ends. The safety clip and the elongated element are designed to attract or repel each other by magnetic force.

13 Claims, 1 Drawing Sheet

(58) Field of Classification Search
CPC ... A61M 5/1626; A61M 5/3213; A61M 5/321
See application file for complete search history.

(56) References Cited

U.S. PATENT DOCUMENTS

| | | | | |
|---|---|---|---|---|
| 6,013,038 | A * | 1/2000 | Pflueger | A61M 25/0169 |
| | | | | 600/585 |
| 2001/0029356 | A1 * | 10/2001 | Vojtasek | A61M 25/0618 |
| | | | | 604/263 |
| 2004/0133167 | A1 | 7/2004 | Ferguson et al. | |
| 2005/0192535 | A1 * | 9/2005 | Takagi | A61M 25/0606 |
| | | | | 604/164.08 |
| 2007/0255211 | A1 | 11/2007 | Young | |
| 2008/0086089 | A1 * | 4/2008 | Isaacson | A61M 5/3273 |
| | | | | 604/164.08 |
| 2009/0012480 | A1 * | 1/2009 | Moulton | A61M 5/3273 |
| | | | | 604/263 |
| 2011/0306937 | A1 | 12/2011 | Andreoni et al. | |
| 2012/0046620 | A1 * | 2/2012 | Woehr | A61M 25/0618 |
| | | | | 604/263 |
| 2012/0130307 | A1 | 5/2012 | Pobitschka | |

* cited by examiner

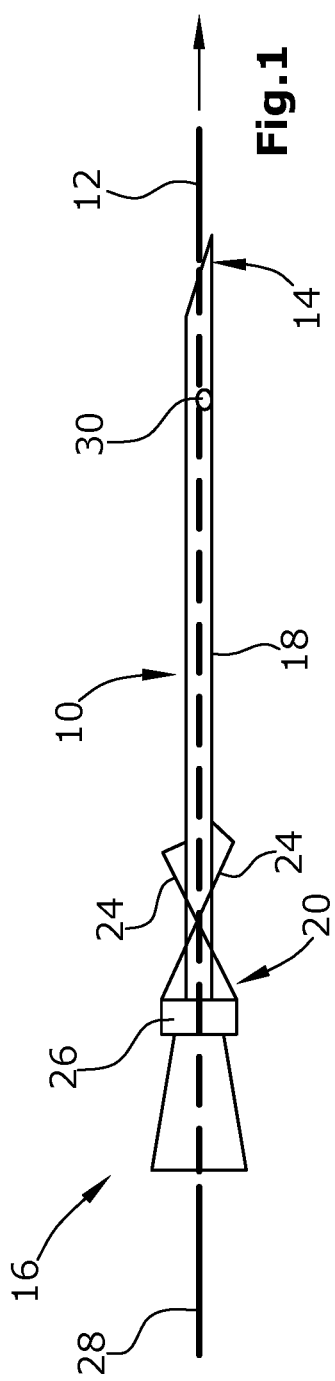
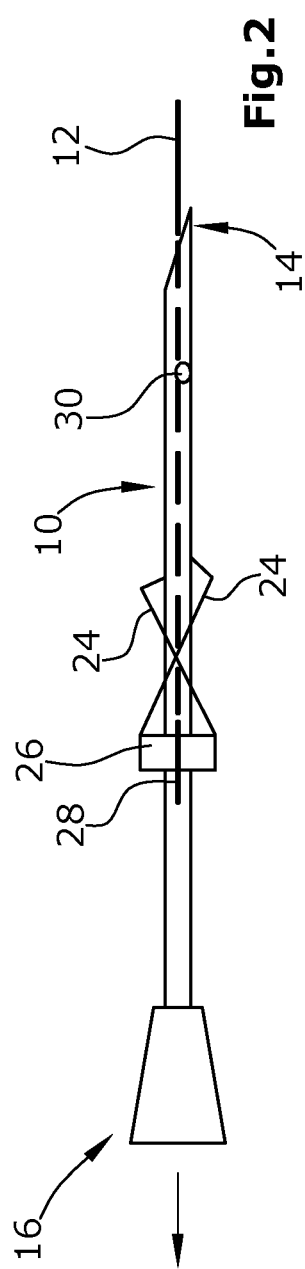
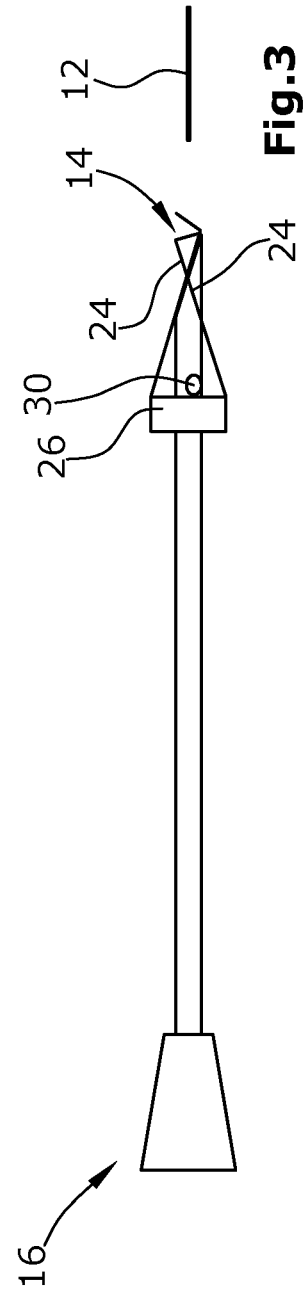

SAFETY CLIP FOR SELDINGER CANNULA

The invention relates to a cannula having an elongated tube, open at both ends, for receiving an elongated element in the form of a wire, a thread or a rod. The elongated element may in particular be a guide wire, and the cannula may be a Seldinger cannula for positioning the guide wire.

A guide wire is used to introduce and position a patient catheter. A frequently used guide wire is a Seldinger wire that is introduced into a patient by means of a Seldinger cannula. For this purpose, the Seldinger cannula has an elongated tube whose opposite ends are open so as to be able to advance the guide wire through the tube. One end of the Seldinger cannula is provided with a tip for insertion into a patient. The other, rear end of the cannula is not provided for insertion into a patient.

For placing the guide wire in a patient, the Seldinger cannula is introduced first by puncturing the patient with the distal tip of the Seldinger cannula. When the end of the Seldinger cannula introduced into the patient is placed correctly in a vessel into which the guide wire is to be introduced, the guide wire is inserted via the rear end of the Seldinger cannula that is not introduced into the patient. The guide wire is inserted completely into the vessel through the Seldinger cannula and is advanced to the intended location. As soon as the guide wire has been placed at the intended position, the Seldinger cannula is pulled from the patient, while the guide wire remains in the patient.

When pulling the Seldinger cannula out from the patient, the distal tip must be covered in order to avoid unintentional stab wounds. In this regard it is known to provide a safety clip enclosing the Seldinger cannula on the outside, the clip being displaceable along the Seldinger cannula. After the Seldinger Cannula has been withdrawn from the patient, the user manually advances the safety clip beyond the distal end of the Seldinger cannula to cover and protect the distal end.

The example of the Seldinger cannula is one of a plurality of possible examples for the use of an elongated element advanced through a cannula. The cannula may be a medical cannula or a catheter. The elongated element may be any element in the form of a cord, a rod or a wire to be introduced into a patient.

It is an object of the present invention to improve the handling of the safety mechanism of a cannula.

The cannula of the present invention is defined by the features of claim 1. The safety clip is designed to engage in magnetic interaction with the elongated element, which interaction leads to magnetic attraction or repulsion between the safety clip and the elongated element. In a variant, the safety clip has a magnetic element or magnetic material magnetically cooperating with the elongated element. As an alternative, the elongated element may comprise a magnetic element or magnetic material magnetically cooperating with the safety clip. For example, the magnetic element may be provided at the end of the elongated element or the elongated element may be entirely made of a magnetic material, e.g. as a wire. In this regard it is conceivable that both the safety clip and the elongated element comprise a magnetic element. As an alternative, the safety clip may comprise a magnetic element and the elongated element may comprise a magnetic material, or vice versa. The magnetic elements may be a permanent magnet of aluminum-nickel-cobalt, a ferrite, Bismanol or neodymium-iron-boron or a solenoid.

According to the invention it becomes possible that, as the cannula is displaced relative to the elongated element, the magnetic interaction between the safety clip and the elongated element exerts a force on the safety clip. In this manner, the safety clip is displaced with respect to the cannula. When the cannula is retracted with respect to the elongated element, the magnetic force displaces the safety clip to beyond the distal tip when the same is withdrawn completely from the elongated element. No manual displacement of the safety clip is required. The magnetic interaction between the safety clip and the elongated element causes the cannula tip to be automatically covered when the cannula same is withdrawn completely from the elongated element.

Preferably, the safety clip is provided with at least one spring arm biased towards the tube interior of the cannula such that upon displacement beyond the tube end, the spring arm springs back into its initial position and thus closes or covers the tube end.

In the region of its distal end, the cannula may be provided with a protrusion or a recess cooperating with the safety clip so as to stop the advance movement of the clip along the cannula. The protrusion or the recess thus forms a stop that blocks the further advance movement of the safety clip. Thereby, the safety clip can be advanced only until the distal end of the cannula is closed, however, without fully detaching the safety clip from the cannula.

The rear proximal end of the cannula is advantageously provided with an enlarged outer diameter so as to stop the advance movement of the safety clip. The enlarged outer diameter forms a rear stop for the safety clip and may for example serve as a funnel to facilitate the insertion of the elongated element into the rear end of the cannula. The safety clip can therefore not be pulled beyond the rear proximal end of the cannula.

The elongated element of the present invention for use with the cannula of the present invention may be provided with an element magnetically cooperating with the magnetic element of the safety clip. The element may for example be a permanent magnet. In this case, the magnetic element of the elongated element is preferably arranged at the rear proximal end thereof. Pulling the cannula from the elongated element beyond the proximal end thereof causes the magnetic element of the elongated element to exert a force on the safety clip and displaces the safety clip towards the distal tip of the cannula.

An embodiment of the invention will be described hereunder with reference to the drawings. In the Figures:

FIG. 1 is a schematic illustration of the embodiment during the advance movement of the guide wire, FIG. 2 illustrates the view of FIG. 1 upon withdrawal of the cannula, and FIG. 3 illustrates the view of FIG. 1 after withdrawal of the cannula.

The cannula 10 is a Seldinger cannula with a cylindrical tube 18 having a front distal end for insertion into a patient and a rear proximal end 16 not to be inserted into the patient. The rear end 16 is enlarged to a funnel shape to facilitate the introduction of the elongated element 12 into the Seldinger cannula 10. The elongated element is a guide wire in the form of a Seldinger wire. In FIG. 1, the guide wire 12 has been passed fully through the Seldinger cannula, i.e. it protrudes from both ends 14, 16.

A safety clip 20 is pushed on the Seldinger cannula 10. The safety clip 20 is pushed on the outside of the tube 18 and is slidable along the tube 18. The safety clip 20 has a magnetic base 26 of a permanently magnetic material. Two spring arms 24 are arranged at the base that are elastically biased in opposite directions in the manner of a pair of scissors or a forceps and towards the tube interior so as to close the distal end 14 of the Seldinger cannula 10 when the spring arms 24 are displaced beyond the distal end 14 as illustrated in FIG. 3.

In the region of the distal end 14, the tube 18 is provided with a recess 30 in the form of a groove forming a stop for the base 26 of the safety clip 20. The base 26 cannot be displaced axially beyond the recess 30. The distance of the recess 30 to the distal end 14 of the tube is smaller than the length of each spring arm 24. Therefore, the spring arms 24 close the distal end 14 when the base 26 abuts the recess 30.

After insertion of the guide wire 12 through the Seldinger cannula 10 and into the patient, the Seldinger cannula 10 is withdrawn from the patient in the proximal direction. A magnetic element 28 of a permanently magnetic material at the rear end of the guide wire 12 not inserted into the patient exerts a magnetic force on the magnetic base 26 of the safety clip 20. In doing so, the magnetic element 28 of the guide wire 12 attracts the magnetic base 26 of the safety clip 20. This magnetic interaction causes the safety clip 20 to stay as close as possible to the magnetic element 28 as the Seldinger cannula 10 is withdrawn from the guide wire 12 of the safety clip 20, as illustrated in FIG. 2. The safety clip 20 is displaced along the tube 18 in the distal direction, i.e. in the direction of the distal end 14 of the Seldinger cannula 10. When the Seldinger cannula 10 is withdrawn completely from the guide wire 12, the safety clip 20 is prevented by the recess 30 from being removed completely from the Seldinger cannula 10. When the base 26 is in contact with the recess 30 the front distal ends of the two spring arms 24 protrude beyond the distal end 14 of the tube. This position is illustrated in FIG. 3. Here, the spring arms 24 have resiliently returned into their natural initial positions and cover the distal end 14 of the Seldinger cannula. In the position illustrated in FIG. 3, the safety clip protects the distal end 14 of the Seldinger cannula so as to avoid stab wounds.

The invention claimed is:

1. A catheter insertion system with an automatic safety feature, the catheter insertion system comprising:
   a guide element having a guide element proximal end and a guide element distal end opposite the guide element proximal end, the guide element defining a longitudinal axis;
   a cannula positioned around the guide element and moveable in translation relative to the guide element along the longitudinal axis, the cannula comprising a cannula proximal end and a cannula distal end;
   a safety clip surrounding an outside portion of the cannula and movable in translation relative to the cannula along the longitudinal axis, the safety clip comprising at least one clip arm having a length; and
   a magnetic element or magnetic material on one of the safety clip and a section of the guide element,
   wherein a magnetic interaction occurs between the magnetic element or magnetic material with the other of the safety clip and the section of the guide element by a magnetic force during a relative movement of the magnetic element or magnetic material along the longitudinal axis,
   wherein, during withdrawal of the cannula from the guide element, the magnetic interaction causes the safety clip to stay close to the guide element while the cannula is movable in translation relative to the safety clip and toward the guide element proximal end, and
   wherein the safety clip automatically covers the cannula distal end when the cannula distal end passes the at least one clip arm during said withdrawal of the cannula from the guide element.

2. The catheter insertion system of claim 1, wherein the cannula comprises an elongated tube, the elongated tube open at both the cannula distal end and the cannula proximal end and configured to receive the guide element.

3. The catheter insertion system of claim 1, wherein the safety clip comprises a base from which the at least one spring arm protrudes.

4. The catheter insertion system of claim 3, wherein the base comprises the magnetic element or magnetic material.

5. The catheter insertion system of claim 1, wherein the at least one spring arm is elastically biased towards an interior of the cannula such that the at least one spring arm resiliently closes the interior of the cannula when the at least one spring arm is advanced beyond the cannula distal end.

6. The catheter insertion system of claim 1, wherein the cannula comprises a protrusion or recess, the protrusion or recess located in a region of the cannula distal end and configured to cooperate with the safety clip so as to limit axial movement of the safety clip along the cannula.

7. The catheter insertion system of claim 6, wherein the protrusion or recess is spaced from the cannula distal end by a distance, the distance being less than the length of the at least one clip arm.

8. The catheter insertion system of claim 6, wherein the safety clip comprises a base from which the at least one spring arm protrudes, the base configured to engage the protrusion or recess to limit axial movement of the safety clip beyond the cannula distal end.

9. The catheter insertion system of claim 1, wherein the cannula proximal end is enlarged to form a funnel.

10. The catheter insertion system of claim 1, wherein the guide element is a guide wire.

11. The catheter insertion system of claim 1, wherein the magnetic element or magnetic material is located on the section of the guide element.

12. The catheter insertion system of claim 1, wherein the at least one spring arm comprises a first spring arm and a second spring arm.

13. The catheter insertion system of claim 12, wherein the first spring arm and the second spring arm are elastically biased in opposite directions, with each of the first spring arm and the second spring arm being elastically biased toward an interior of the cannula.

* * * * *